US006547826B2

(12) United States Patent
Matapurkar

(10) Patent No.: US 6,547,826 B2
(45) Date of Patent: Apr. 15, 2003

(54) METHOD OF ORGANOGENESIS AND TISSUE REGENERATION/REPAIR USING SURGICAL TECHNIQUES

(75) Inventor: Balkrishna Ganpatrao Matapurkar, New Delhi (IN)

(73) Assignee: Maulana Azad Medical College, New Delhi (IN)

( * ) Notice: Subject to any disclaimer, the term of this patent is extended or adjusted under 35 U.S.C. 154(b) by 0 days.

(21) Appl. No.: 09/792,652

(22) Filed: Feb. 23, 2001

(65) Prior Publication Data

US 2002/0007223 A1 Jan. 17, 2002

Related U.S. Application Data

(63) Continuation-in-part of application No. 08/921,307, filed on Aug. 29, 1997, now Pat. No. 6,227,202.

(30) Foreign Application Priority Data

Sep. 3, 1996 (IN) ........................................ 1959/DEL/96

(51) Int. Cl.⁷ ................................................ A61F 2/02
(52) U.S. Cl. ................................................ 623/23.72
(58) Field of Search .......................... 623/23.64, 23.65, 623/915, 23.72

(56) References Cited

U.S. PATENT DOCUMENTS 6,077,987 A * 6/2000 Breitbart et al. ............... 623/11

OTHER PUBLICATIONS

Gearhart, J., "New potential for human embryonic stem cells", Science, vol. 282, Issue 5391, pp. 1061–1062.*
Fenoglio–Preiser, C.M. et al., "Gastrointestinal Pathology An Atlas and Text", Second Edition, pp 1–14, 1999.
Creighton, T. E., "Encyclopedia of Molecular Biology", vol. 4, pp 2430–2433, 1999.
Potten et al., *Development 110*, "Stem cells: attributes, cycles, spirals, pitfalls and uncertainties Lessons for and from the Crypt", pp1001–1020, 1990.

* cited by examiner

Primary Examiner—David H. Willse
Assistant Examiner—Javier G. Blanco
(74) Attorney, Agent, or Firm—Merchant & Gould P.C.

(57) ABSTRACT

A method of isolating and developing a membrane containing pluripotent autogenous stem cells of endodermal origin for the use of neo-organogenesis and neo-histogenesis of various organs and tissues in mammals.

12 Claims, 14 Drawing Sheets

Figure 1E:
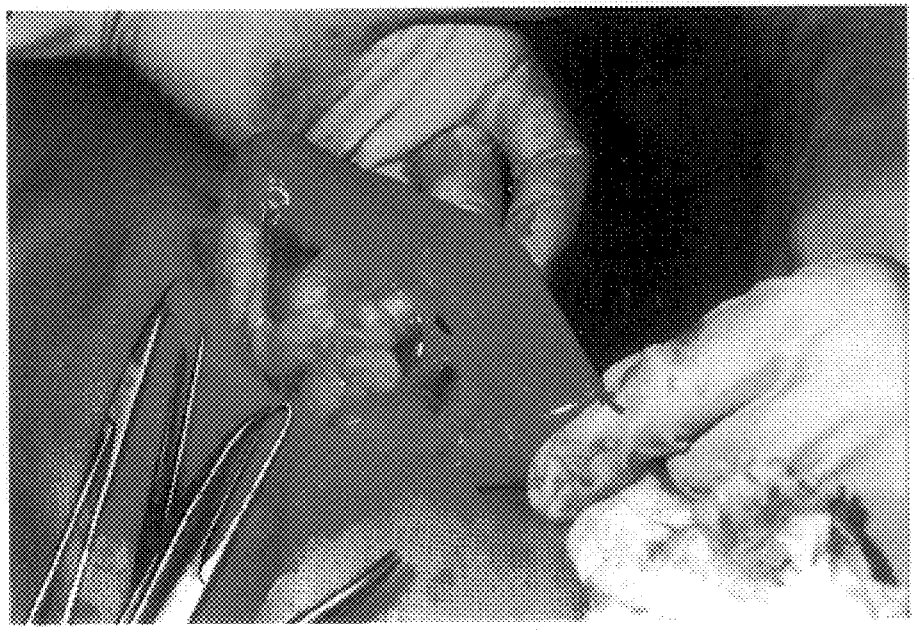

(9 of 14 Drawing Sheet(s) Filed in Color)

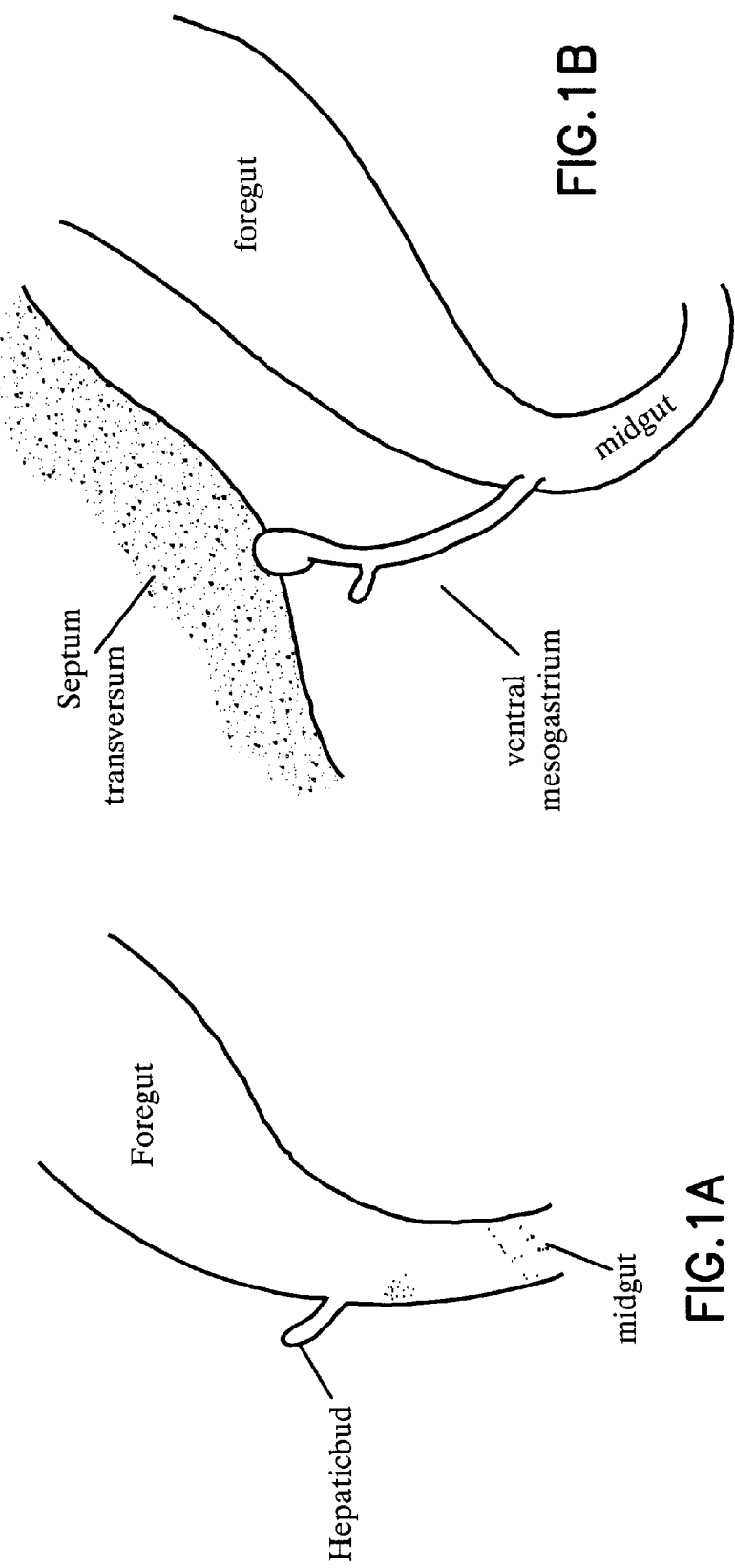

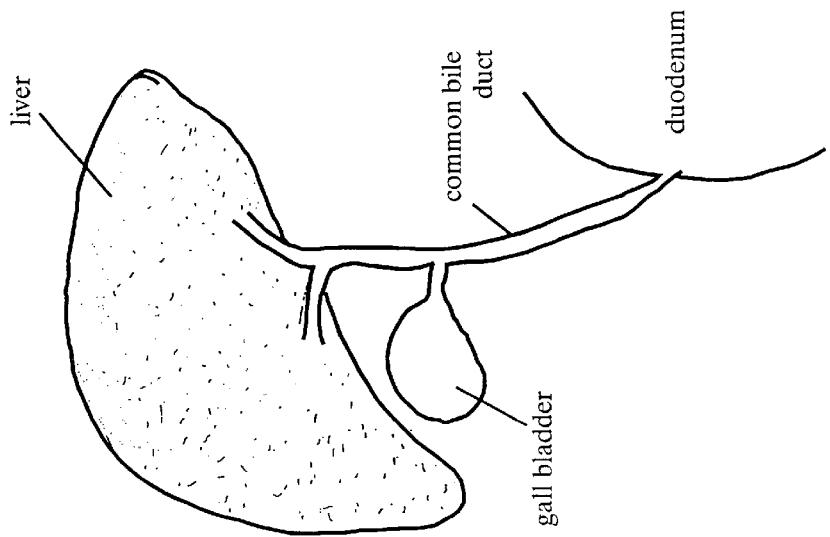
FIG. 1(D)
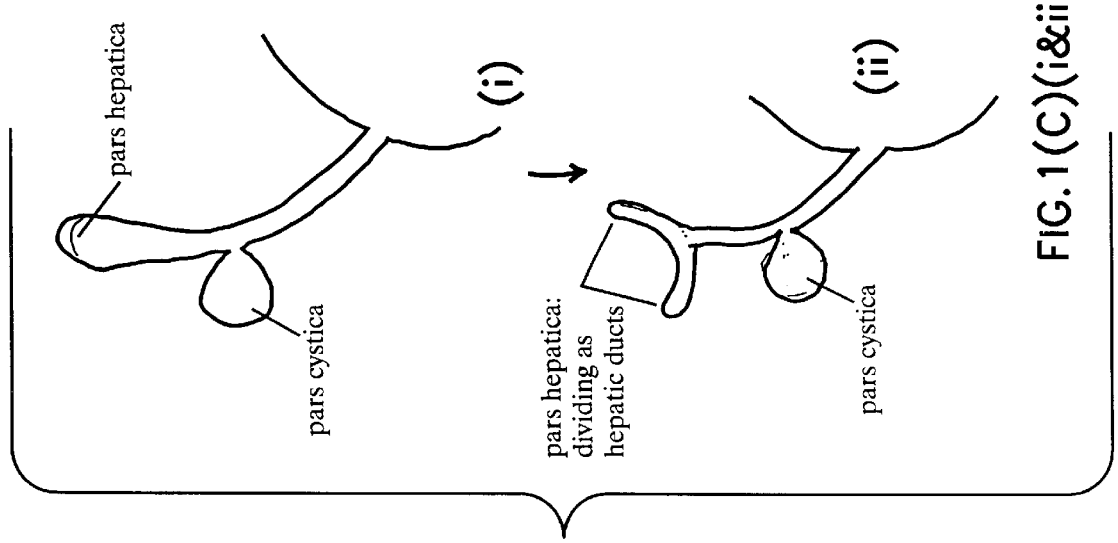
FIG. 1(C)(i&ii)

US 6,547,826 B2

METHOD OF ORGANOGENESIS AND TISSUE REGENERATION/REPAIR USING SURGICAL TECHNIQUES

The present application is a Continuation-in-part of U.S. application Ser. No. 08/921,307 filed on Aug. 29, 1997 now U.S. Pat. No. 6,227,202 B1, the disclosure of which is incorporated herein by reference.

FIELD OF THE INVENTION

The invention relates to organogenesis, i.e. repair and/or neo-regeneration of tissues and organs in a mammalian body utilising autogenous stem cells of developed tissues. Particularly, the method of the invention is useful to regenerate or repair organs of endodermal origin such as bile duct, urinary bladder etc in vivo.

DEFINITIONS

Some of the terms used in the specification are defined herebelow for better understanding and clarity.
1. 'Organogenesis': is a term Generally used in embryology; it denotes the formation of organs from the fertilised ovum in developing embryo.
2. 'Neo-Regeneration' in biological terms means restoration of lost structures of a tissue organ or the tissue/organ itself. As used herein, the term includes restoration of not only the tissue or structures thereof, but also an attempt to restore functions performed by the tissue/organ.
3. Histogenesis: Formation of tissues of the body.
4. Plasia: Growth or a change (Latin—To mould).
5. Metaplasia: Change of cells from normal to abnormal state (Latin-Meta+plasia). Thus, transformation of a fully developed tissue into another fully developed tissue is known as metaplasia.
6. Desired Metaplasia: It is a kind of Metaplasia, but the transformed tissue containing stem cells is useful, needed, desired and compatible anatomically, physiologically and histologically, in the new region of exposure and is responsible for neo-regeneration of tissues and organs.
7. Stem cells: These cells are a kind of primitive cells present in an embryo or an adult body and have the capacity to differentiate into specialised tissues, having different functions. These cells can be defined in terms of their functional capabilities. Stem cell is not a property but a spectrum of capability.
8. Regeneration: The growth of destroyed or devitalised tissue or organ from the remnant tissue or organ. It is a reparative attempt of the body. This regeneration is different from neo-generation as it does not involve formation total tissue or organ and is not by colonisation or grafting tissue or cells which in turn undergo transformation and form new tissue.
9. Neo-organogenesis: Formation of tissue or organ by the transformation of stem cells on colonisation by differentiation and proliferation.
10. Neo-histogenesis: Formation of tissues by differentiation and proliferation of stem cells on colonisation in the tissues.
11. Contiguous embryonal segment: It is the region in an embryo from where the donor and recipient tissue/organ have developed and the same region corresponds in the adult/developed body.
12. Adult or developed body: Animal body where embryonal morphogenesis is complete and is capable of independent existence even though same tissues/organs may be still developing or adulthood has reached. Hence, the term "developed body" as used herein denotes a body in which embryonal morphogenesis is complete.

BACKGROUND OF THE INVENTION

In nature, plant life and lower animals display the capacity to re-grow their lost tissues and organs. For example, newts can grow their amputated eye lens, lobsters and crabs can grow their broken claws, lizards can grow their severed tails and frogs can grow their amputated legs.

Basic laws of nature remain hidden in the revealed world of nature. It is known that a fertilised egg undergoes various stages of morphogenesis and develops into an embryo and eventually into an adult. Morphologically, the early embryos of different species are strikingly similar. At this early stage of development of embryo it is difficult to differentiate between the embryos of different species, and one cannot say which embryo will become fish, bird, dog, pig, monkey or man. Thus, a single celled ovum forms an adult body having different organs and tissues with different structure and function. Multicellular bodies of higher life forms are formed by differentiation of and proliferation of embryonal primitive germ cells. In order to sustain complex life functions, the cell specialisation has to be maintained and thus, organ regeneration capacity is compromised in higher forms of life due to specialisation of stem cells and maintenance of specialisation.

The laws of nature are difficult to understand but have uniform applicability, in nature. Therefore, if lower life forms can re-grow lost parts, the applicant believes that such capacity may be present in higher life forms as well. As such, there are numerous attempts in the prior art to regenerate tissues and organs, each with variable rates of success. Some attempts comprise isolation of tissues from pigs and culturing the same to regenerate organs like liver or kidneys, in vitro. The major disadvantage with in vitro procedures is that they are very expensive, and therefore, not always affordable. Besides, there is always a problem of revascularization and acceptance of the organ regenerated in vitro by the human body. In other words, organ transplantation though a successful process, is plagued by rejection phenomenon which needs life long use of immunosuppressants. This not only increases the cost but jeopardises the host immunity. Non-availability of suitable donor, preservation and transportation of organ are a few other problems associated with organ transplantation. Hence, it is always preferable to exploit the body's own potential to restore lost tissue/organs.

It is known that a fertilised ovum undergoes a series of divisions and forms a germ-layered disc. This disc consists of ectoderm, endoderm and mesoderm. These germ layers independently or in combination form various tissue and organs of an adult body. The endoderm of the embryonic germ disc forms a cavity lined by the cells of endodermal origin called 'primary yolk sac'. A part of the cavity of the yolk sac is enclosed within the embryo to form the primitive gut, this gut is in free communication with the rest of the yolk sac. The part of the gut cranial (proximal) to this gut is the fore-gut; the part caudal is the hind-gut, while the intervening part is the mid-gut. The formation of these layers of the germ disc is attributed to the totipotent nature of the cells of the fertilized ovum. With the formation of the germ layers of germ disc, the cells lose their totipotent nature and become pluripotent, and as a consequence, these cells of the germ layers cannot form the whole body, but can only form certain tissues and body systems, derived from that specific germ layer. Thus, differentiation and specialisation of germ layer cells leads to specialised organ and tissues formation. Reverse activity i.e. formation of germ layer cells by the specialised tissue cells is not observed. Therefore, it is understood that the neo-regeneration of tissues requires pluripotent stem cells.

It is interesting to note that the stem cells developed from a particular layer of germ disc of developing embryo are present in some places in the developed tissues of adult body. These cells do maintain their pluripotent nature. In fact, "stem cells" by their great proliferative property maintain differentiated cell populations throughout the life of an animal (Ashman L. 1999, Stem Cells Encyclopedia of Molecular Biol. Vol.4. Ed. By TE Geighton, Publishers: John Wiley & Sons Inc. NY, Chichester, Weinheim, Brisbane, Singapore, Torento P. 2430–2433). The large division potential makes these cells efficient tissue regenerators through clonal growth (C.S. Potten MS Loeffler. Stem Cells; Attributes, cycles, spirals, pitfalls and uncertainties, lessons, far and from the crypt Dev. 110–1001–1020=1990. Review article). However, the exact loci where these stem cells are situated in an adult or developed body is not known.

The Applicant worked and used the principle that stem cells still exist in the adult body and retain their capacity to form various tissues given the right kind of environment and stimuli. The applicant has noted that the stem cells present in the developed body have lost their capacity to migrate because the development in the adult body is fixed on localised. Hence, the applicant has used the inherent capacity of stem cells to proliferate, differentiate and form specialised tissues/organs in the required sites by transporting the stem cells to the desired sites by way of surgery. For this purpose, the applicant has first identified the embryonal germ layer in the embryo, from which the organ to be repaired or regenerated has developed. In other words, the applicant has identified the embryonal germ layer responsible for the origin of the organ desired to be regenerated or repaired. Then, the Applicant has identified the region in the developed body where the stem cells of that particular germ layer are situated. A membrane containing these cells is grafted onto the site or the organ which is to be regenerated or repaired. Using this principle, the Applicant has successfully regenerated various organs and tissues, developed from embryonic mesoderm in his earlier accepted and pending U.S. application Ser. No.08/921,307. The applicant has now used similar principles to regenerate various organs that have resulted from the differentiation and proliferation of pluripotent cells of the endoderm.

OBJECTS OF THE INVENTION

The main object of the invention is to provide an in vivo and in situ method for regeneration or repair of organs and tissues in mammals such as humans.

Another object of the invention is to provide an in vivo and in situ method for regeneration or repair of endodermal organs and tissues in mammals such as humans.

Another object of the invention is to provide a method for regeneration or repair of organs, eliminating the problems of organ transplantation such as non-availability of organs, rejection of transplanted organs by the recipient host, life long use of immunosuppressents by the recipient, need of perfect tissue matching etc.

Still another object is to provide a method for regeneration of organs, that utilises autogenous tissues.

One more object of the invention relates to effective management of diseases of organs.

Yet another object of the invention is to provide a cost effective method of regeneration of organs without any need for donor or costly equipments or costly nutrients to promote growth of cells.

Still another object of the invention relates to use of autogenous tissues so that the use of immunosuppressents is eliminated to prevent rejection phenomenon common in organ transplant surgery.

A further object of the invention is to utilise the phenomenon of 'desired metaplasia' of tissues i.e. providing useful transformation of one tissue into required tissue(s).

Yet another object of the invention is for providing regeneration or repair of organ tissues employing stem cells in vivo.

One more object of the invention relates to the regeneration or repair of various organs/tissues of the body employing relevant stem cells from autogenous tissues present in various parts of the body.

Still another object of the invention relates to regeneration of organs/tissues by surgically transferring stem cells to the region of the organ/tissue system were regeneration is required.

Furthermore, the invention relates to regeneration of bile duct, urinary bladder from the embryonic contiguous regions of endoderm.

SUMMARY OF THE INVENTION

This invention relates to a method of isolating and developing a membrane containing pluripotent autogenous stem cells of endodermal origin for the use of neo-organogenesis and neo-histogenesis of various organs and tissues in mammals.

DETAILED DESCRIPTION OF THE INVENTION

The invention relates to a method for repair or regeneration of organs and tissues that have originated from the endodermal plate of the germ disc of developing embryo. Thus, the invention provides an in-vivo method of neo-organogenesis of various tissues or organs developed from endodermal germ layer, in a mammalian body, comprising the steps of surgically transferring an autogenous membrane containing stem cells to the site of the organ or tissue of endodermal origin, to be regenerated, said membrane being selected from the corresponding contiguous embryonal segment in a developed body and providing the functional need and tissue environment for regeneration of the desired tissue or organ.

In general, the method in vivo and in situ for regeneration or repair of organs, comprises the following steps:
i) identifying the embryonal germ layer responsible for the origin of the organ to be regenerated or repaired, and the corresponding contiguous embryonal segment in a developed body,
ii) isolating an autogenous membrane containing pluripotent stem cells from the identified site, wherein the stem cells in the membrane are rendered free of the influence of the local anatomical tissue environment,
iii) surgically transferring the said autogenous membrane to the region where repair or neo-regeneration of the organ is desired, and
iv) providing appropriate stimuli and sufficient time for differentiation and proliferation for neo-regeneration.

The tissue from which the autogenous cellular membrane is obtained may be termed as the 'donor tissue' for ease of reference and the tissue or organ to be regenerated or to which region or locus, the donor tissue cells are grafted or colonised, may be termed as 'recipient tissue'.

An important aspect is that the donor and recipient tissues should essentially be derived from the same germ layer in an embryo. Each of the tissues and organs of the human body owe their origin to different germ layers of the germ disc of the embryo. For example protective tissues viz. Skin and nerve tissues are ectodermal derivatives, lining of the epithelium and exocrine glands originate from the endoderm, while cardiovascular, genito-urinary and other systems are formed from the mesoderm. Similarly, the gut originates from the endoderm. Parts of the gut such as the trachea also originate from the endoderm. It is observed that the donor and recipient tissues must be selected from the neighbouring regions in a developing embryo. This enables proper neo-regeneration. Graft survival is possible only when donor and recipient tissues in question originate from the same geim layer in the embryo. Stem cells' response to Extra Cellular Matrix cytokine signalling is matched and compatible. Therefore, for desired metaplasia to take place, cell potential, environment and functional need are all essential. In the present invention, the organs to be repaired or regenerated develop from the endodermal layer of the germ disc of the embryo.

The donor tissue selected is such that it is replete with stem cells preferably of pluripotent nature. If the cells do not have the potential to differentiate and proliferate in different path ways, desired metaplasia may not initiate at all and neo-regeneration of total tissue or organ may not be possible. The autogenous membrane or the donor tissue is characterised by the presence of stem cells which when exposed to the environment of the recipient tissue, are capable of reacting with tissue organisers and enable regeneration of organs. The autogenous membrane isolated from the identified site is characterised in that it is rendered free from influence of local anatomical tissue environment and are made available for differentiation and proliferation in the site where regeneration/repair of the organ is desired. Thus, the stem cells become readily receptive to the new environment which has been provided by surgical transfer i.e. the site of exposure (site of recipient tissue) where repair or neo-regeneration is desired. The stem cells of the autogenous membranes are made susceptible to the action of the local tissue organisers (induces, inhibitors, etc.). Pluripotent nature of stem cells helps in formation of all the histological components of the tissue or organ. Stem cells have capacity to survive indefinitely and independently in the tissues. These cells have coded memory in RNA and can synthesize their own new protein and thus are capable of differentiation and proliferation in different pathways. The intrinsic factors such as messenger gene and genetic factors, inherent in the stem cells is exploited for regeneration or repair of the desired organ. Accordingly, these cells have potential for neo-regeneration of tissues. These cells during differentiation also maintain stem cell character in one progeny while other is differentiating. Therefore, presence of stem cells in donor tissue is an important criteria for neo-regeneration.

When the autogenous cellular membrane is transferred to the site of repair/neo-regeneration of the concerned organ, the said membrane is faced with a new environment with new functional needs. The step of providing functional need includes creating a stress of new functional need of the tissue system of new location to which stem cells have been shifted, to induce desired metaplasia. It is the applicants' finding that the cytokines in the region of the recipient tissue acton the cells of the autogenous membrane, especially the stem cells, and thus trigger the differentiation and proliferation of the stem cells in the membrane into desired cells required in the region, resulting in the neo-regeneration or repair of the organ. Some of the factors responsible for stem cell proliferation are messenger genes, genetic factors, instrinstic capacity and messages coded in the stem cells.

Cell surface receptors have specificity of response to specific cytokines. Therefore, compatibility of Cell Surface Receptors of the donor tissue should match with that of the surrounding tissues (recipient tissues).

Time: Time is yet another important factor. Once the donor tissue is grafted to the recipient time or organ, the graft should be allowed to develop/mature for a period sufficient to enable regeneration of organs. The period varies from organ to organ: in general, a period of at least 3 to 5 months should be allowed for the organ to regenerate/develop. This is because time is taken for cellular response to exhibit the outcome. This is needed for synthesis of required protein, differentiation and proliferation, etc.

The organ regenerated contains all the layers of cells as in the original organ. The shape and histological structure of the regenerated organ is also found to be identical to that of the lost original organ. The organ so regenerated or repaired is capable of performing all its functions.

In an embodiment the muscosal surface of isolated membrane is kept towards the lumen of the organ to be regenerated/repaired. Also, a support is placed inside the autogenous membrane to counter act the abdominal pressure exerted. The ends of the tubular graft and the CBD are spatulated before anastomosis to avoid constriction at the anastomosed site.

In another embodiment the organogenesis of various tissues/organs incorporates functions of tissue inducers and/or tissue organisers to achieve regeneration/repair of any tissue or organ into its proper size, shape and form to perform its inherent function.

The Applicant has successfully used the aforementioned principles to regenerate several organs that owe their origin to the embryonic endoderm. Two specific examples are illustrated herein—the regeneration of bile duct and urinary bladder. These examples should not be construed as limitations on the inventive scope embodied herein.

The file of this patent contains at least one drawing executed in color. The Patent and Trademark Office will provide copies of this patent with color drawings upon request and payment of the necessary fee.

The invention is illustrated by the following photographs and diagrams:

FIGS. 1(A) to (D): are diagrammatic representations of development of common bile duct in embryo.

FIG. 1(E): shows the normal duodenum. A part (between arrows) isolated and excised after Ligating Blood Vessels between Pancreas (P) and Duodenum(D).

Figure 2:
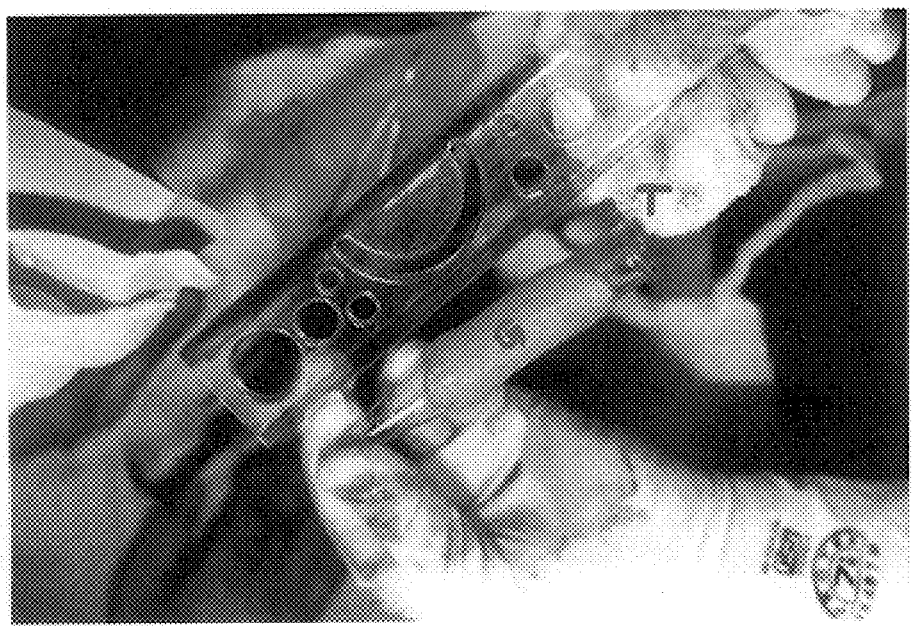

FIG. 2: shows the isolation of stem cell membrane. The excised gut(G) is freed from mucosa and serosa muscularis externa by sharp and blunt careful dissection after ensleeving on conical centrifuge tube (T). The gut tube is turned inside out for dissection of mucosa. After removal of part of mucosa the tube is turned out side in so that mucosal surface faces inside the lumen again.

Figure 3:
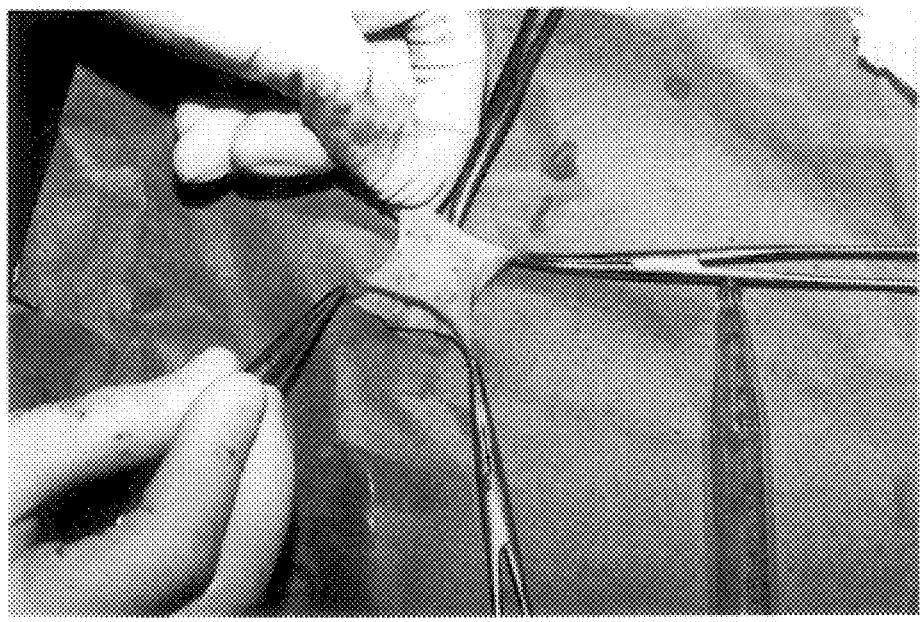

FIG. 3: shows the membrane cylinder of Recto-Sigmoid junction (Hind Gut). Thin tough bluish membrane seen with brown spots on muscosal surface.

Figure 4:
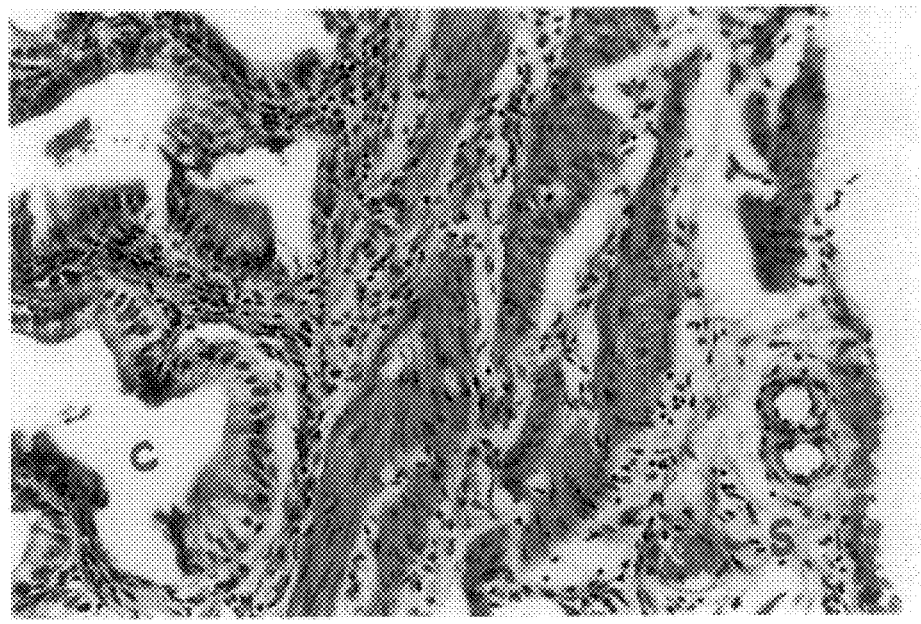

FIG. 4: represents the cellular details of the harvested membrane. It shows Haematoxylene and eosin (H&E) stained 10×10 magnification of duodenal wall. Bases of crypts(C) over thin layer of muscularis mucosa (MM) and part of sub mucosa(S) with Blood vessels, Rest of the sub mucosa, muscularis externa and serosa excised. The normal healthy cells with nuclei are seen in crypt bases(C).

Figure 5:
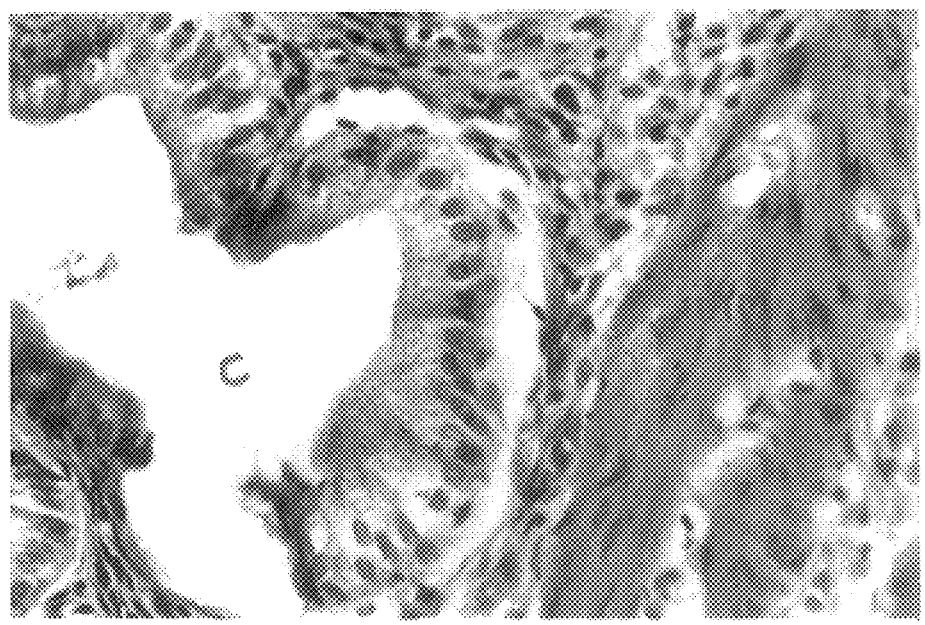

FIG. 5: represents the cellular details of the harvested membrane. It is a HE stained (10×40 magnification) of isolated membrane of duodenum. Note cytoplasm containing granules in the cells of base of crypt.

Figure 6:
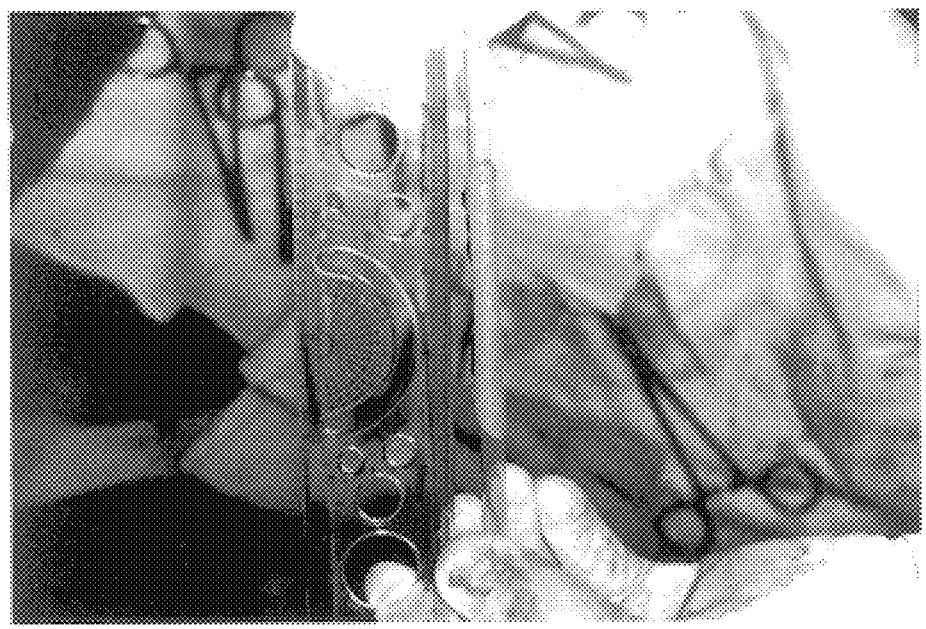

FIG. 6: shows the isolated membrane (from duodenal part of foregut). A tube is constructed out of membrane for the use in the regeneration of Common Bile Duct.

Figure 7:
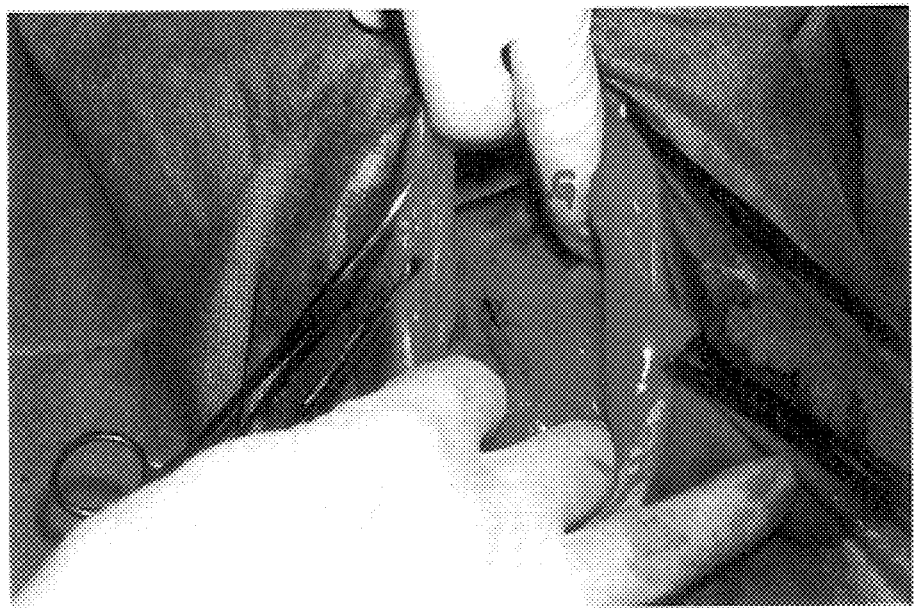

FIG. 7: shows the use of isolated membrane tube in place of Common bile duct. Proximal anastomatic line (A) near Gall Bladder (G) and Common Bile Duct (C) Displays enough place for 'T'–Tube Drainage. Horrizonal Limb as a stent in graft tube.

Figure 8:
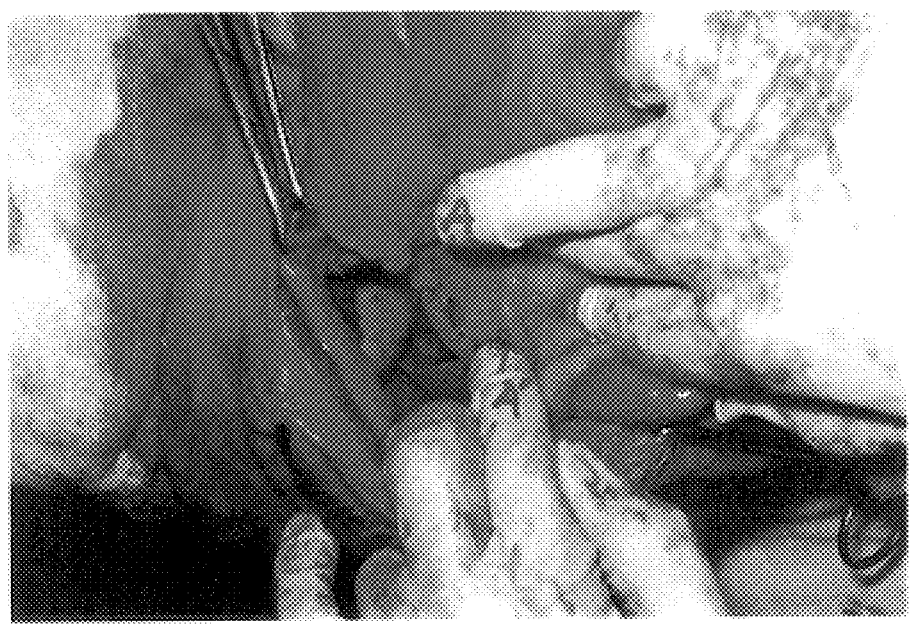

FIG. 8: shows the membrane tube (T) anatomosed to excised CBD (C). Note anostomotic lines A and A'. No place for proximal T. Tube drainage but enough place for T. tube drainage on distal CBD.

Figure 8A:
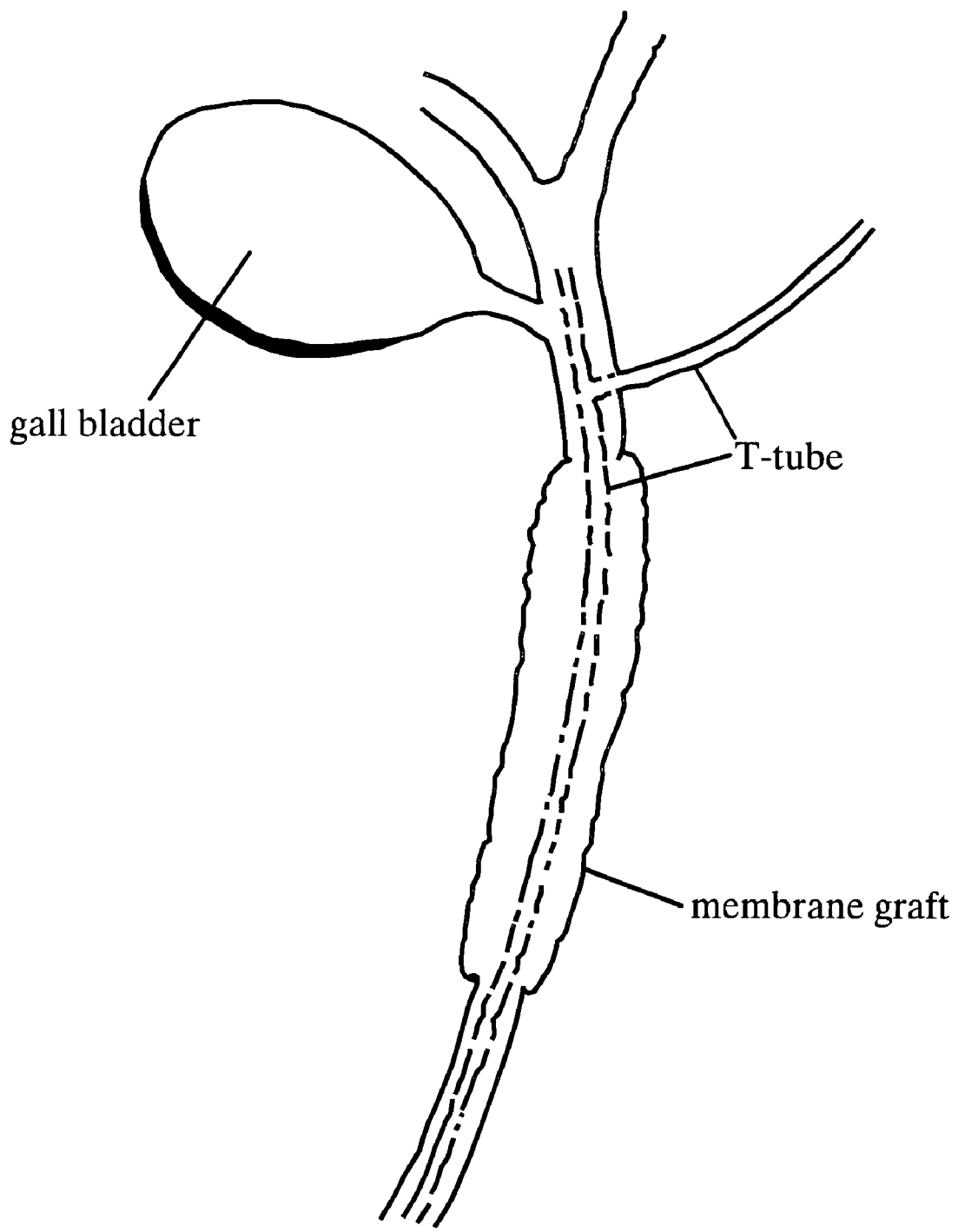

FIG. 8(A): shows the diagrammatic representation of technique of anastomosis of membrane graft with common bile duct and T-tube drain as stent.

Figure 9:
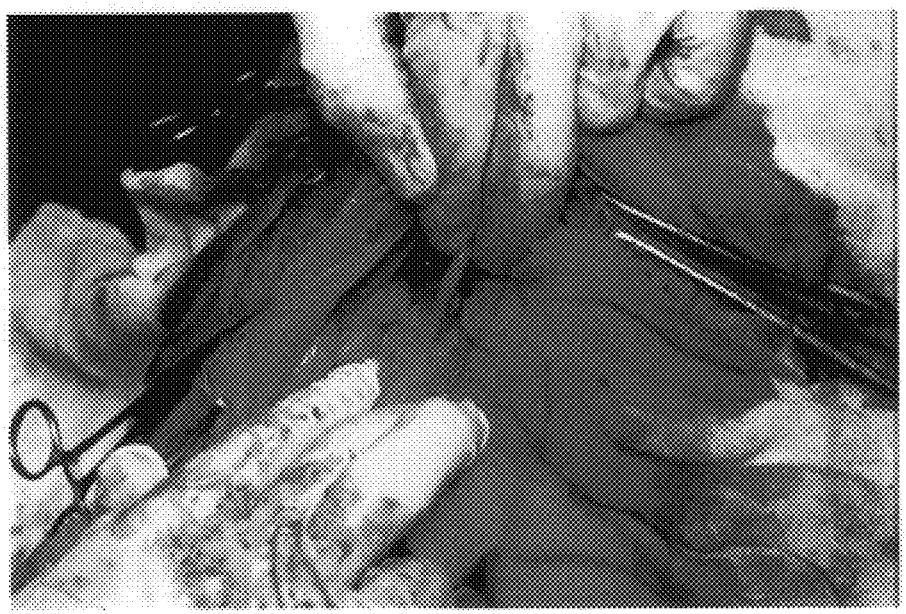

FIG. 9: shows the isolated membrane tube: [3 months post operative]: Showing distal anatomotic line with distal cut end of common Bile duct (A).

Figure 10:
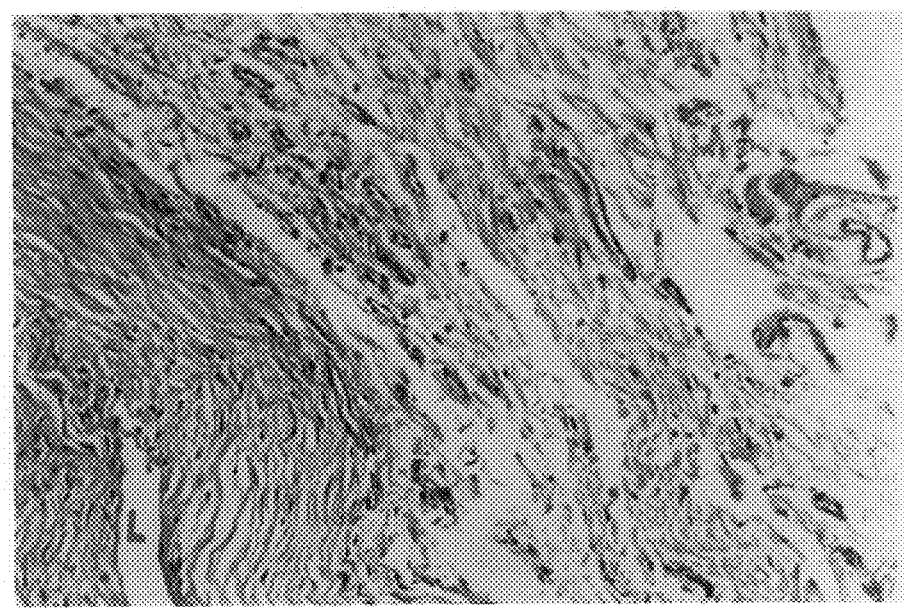

FIG. 10: Common Bile Duct: [Histology]: Isolated membrane graft after 3 months post operative period in common bile duct. [HE stain 10×10 magnification] Lumen (L) & Fibro-muscular wall. M.T.S stained sections microscopically showed only a few smooth muscles. Comparable with normal bile duct structure.

Figure 11:
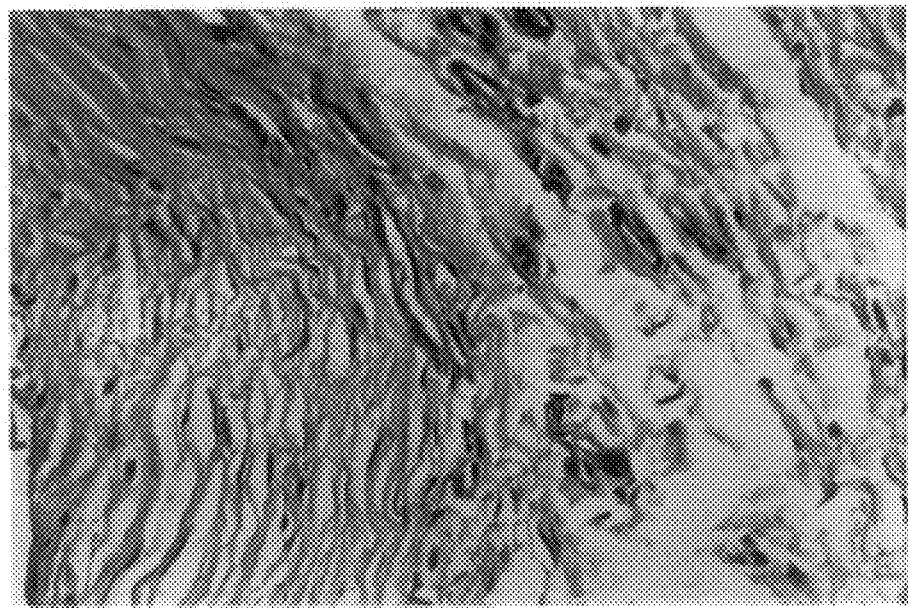

FIG. 11: Bile duct continued: High power 10×20 magnification to show fibromusclar tissue wall developed in the graft membrane after three months of postoperative period.

Figure 12C:
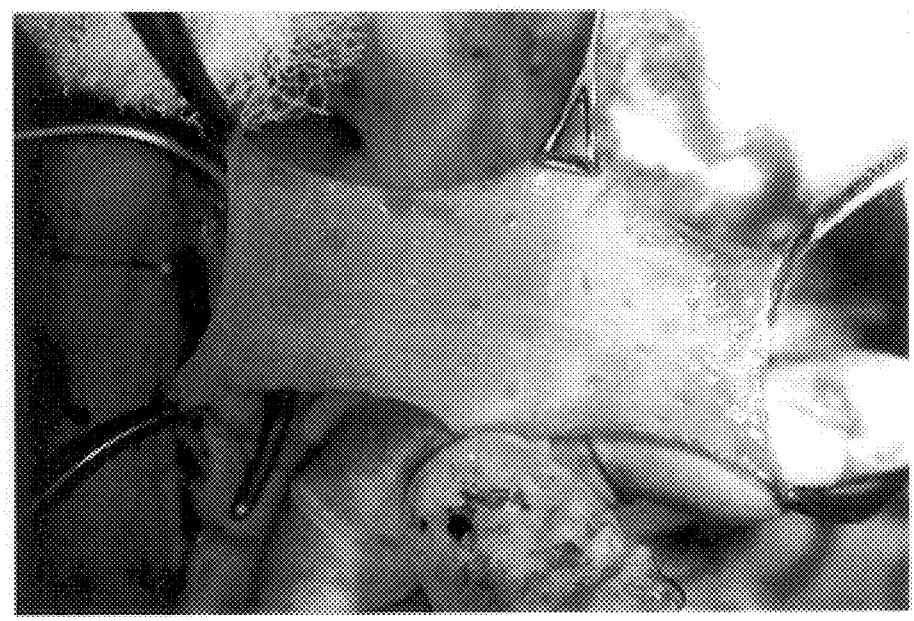
Figure 12A:
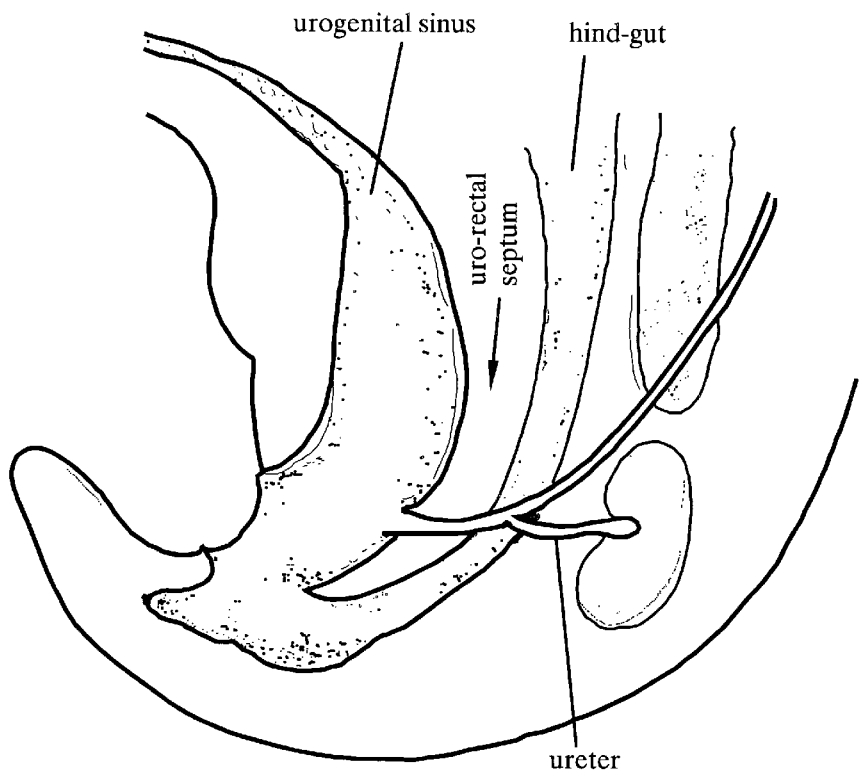

FIGS. 12(A) and (B): shows a diagrammatic representation of development of urinary bladder and rectum by growth of uro-rectal septum.

FIG. 12(C): The isolated membrane [Rectosigmoid region] is thin but tough. The visible spots are crypt openings (Magnified view). The membrane is without any perforation. The Cylinder of membrane of FIG. 3 is slit to obtain flat membrane. It is used for suturing on excised Urinary Bladder. It can be tailored as needed.

Figure 12B:
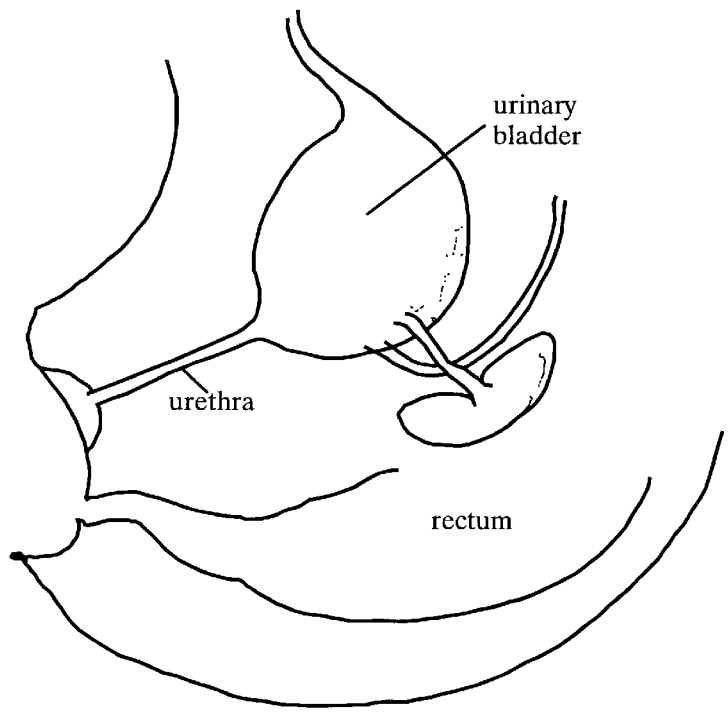
Figure 12D:
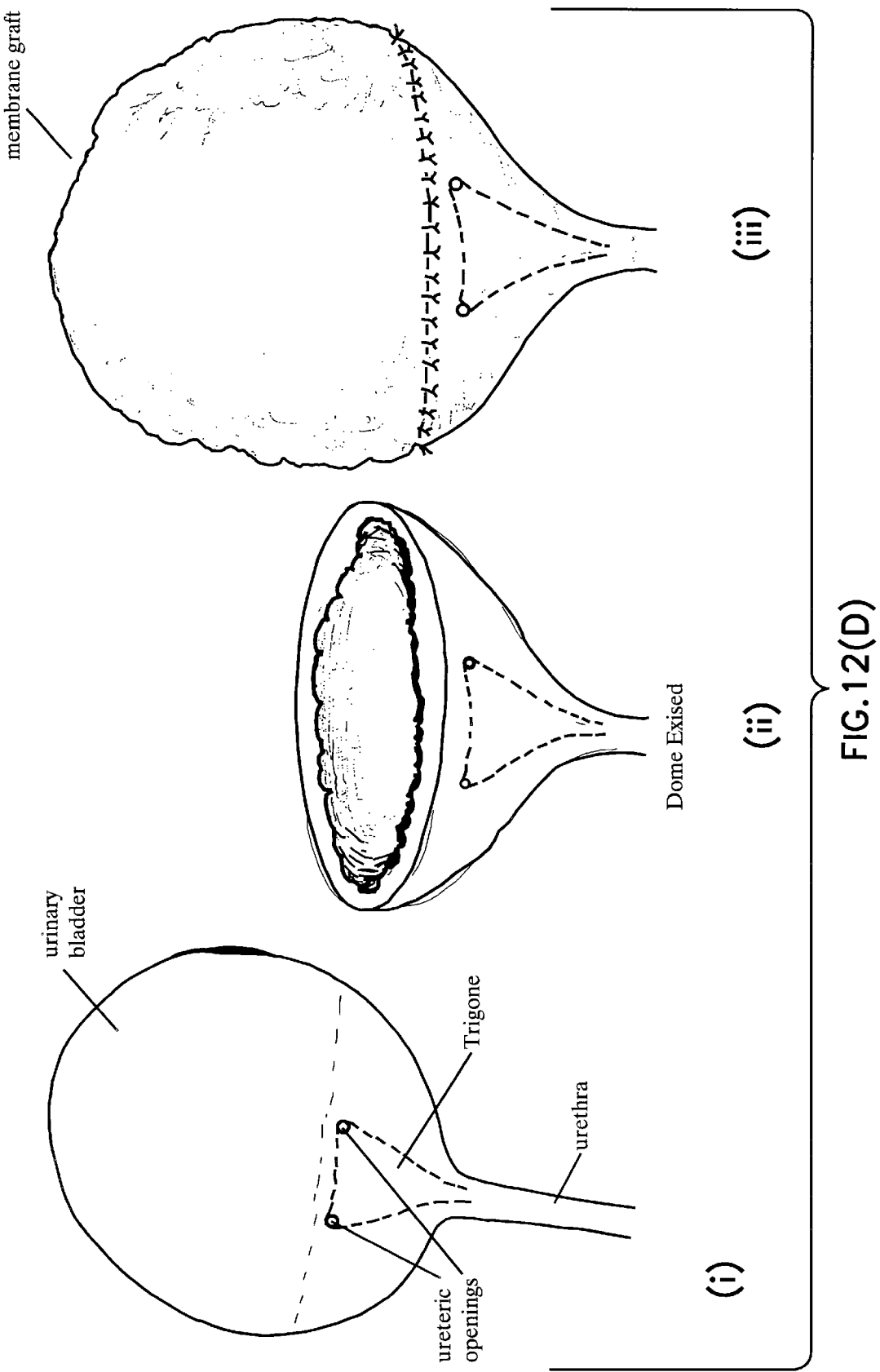

FIG. 12(D): shows diagrammatic representation of technique of excision of dome of urinary bladder and anastamosis with isolated membrane.

Figure 13:
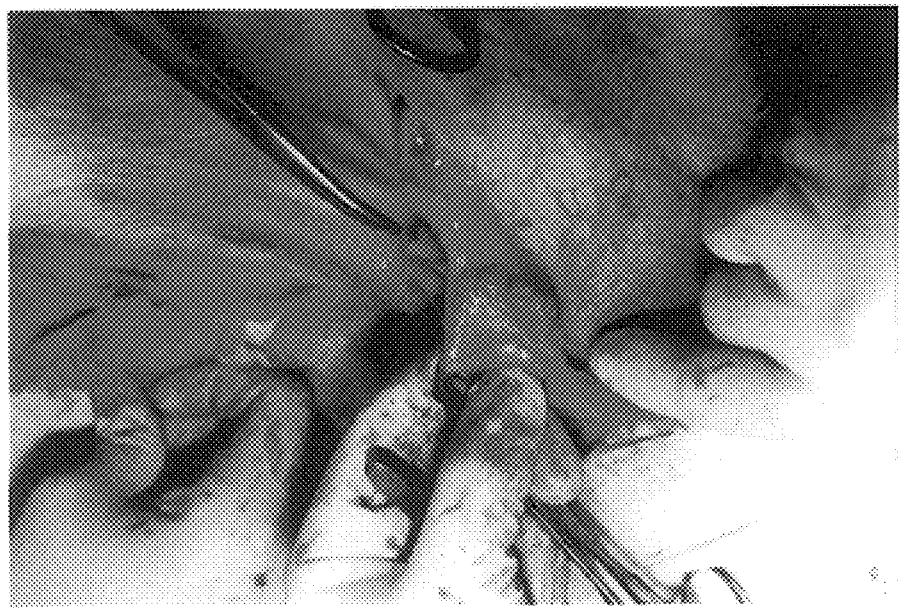

FIG. 13: Dome of Urinary Bladder excised and replaced with isolated harvested membrane. A water proof anastamosis is carried out. Capacity of Urinary Bladder measured by measuring amount of saline it can hold (150:200 ml of saline).

Figure 14:
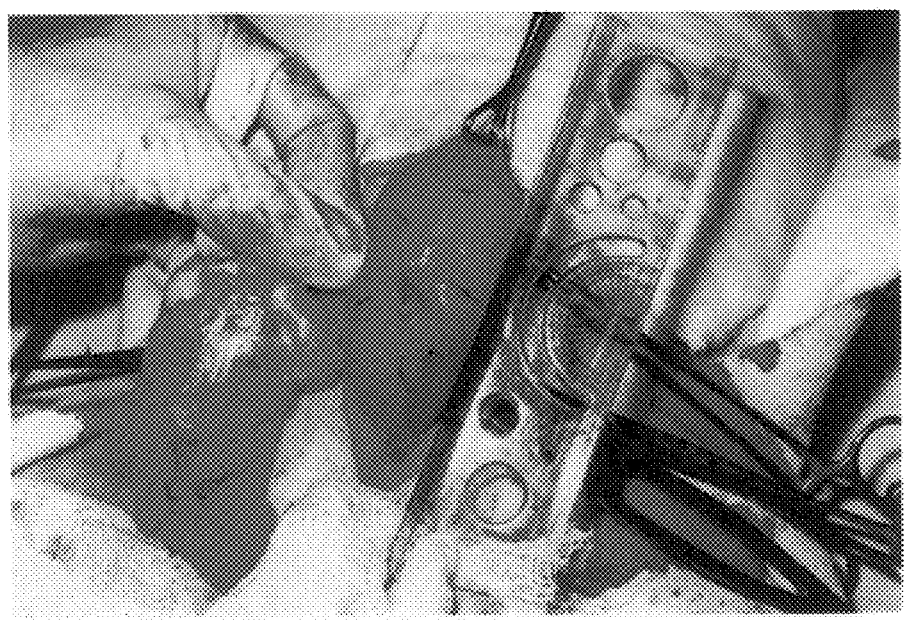

FIG. 14: Urinary Bladder after 3 months post operates period. Markers seen on anastomatic line. See the rough area of adhesions of omentum on the membrane anastomosed with Urinary Bladder in the centre.

Figure 15:
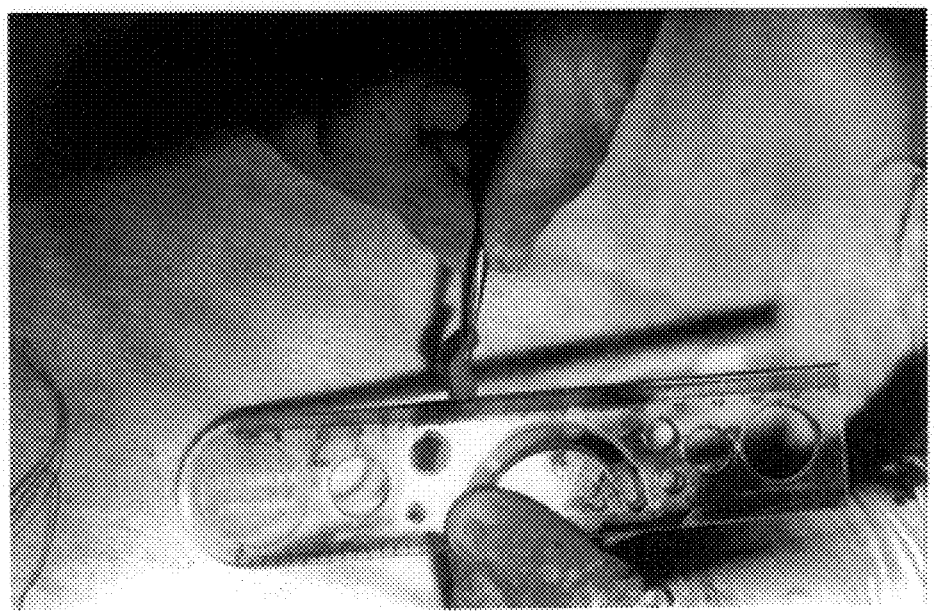

FIG. 15: Urinary Bladder: Isolated membrane after 3 month on Urinary Bladder. Note the thickness. The thin membrane because 0.4 to 0.5 mm thick after 3 months of colonisation on Urinary Bladder.

Figure 16:
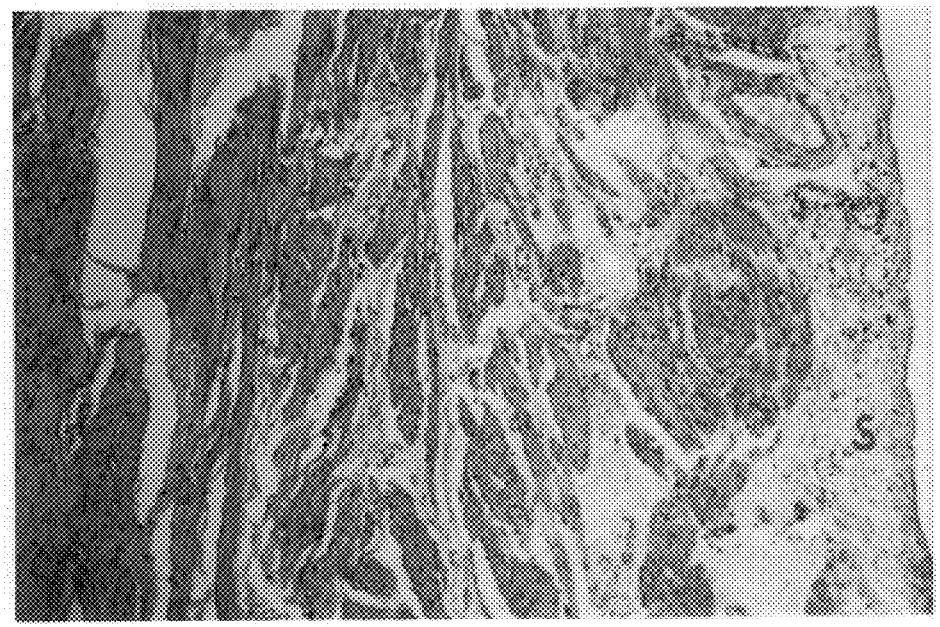

FIG. 16: Urinary Bladder Continued: histology: H&E stain, 10×10 magnification: Isolated membrane 3 months post operative period. Well developed serosal layer(s) and sparce smooth muscles (compare with normal).

Figure 17:
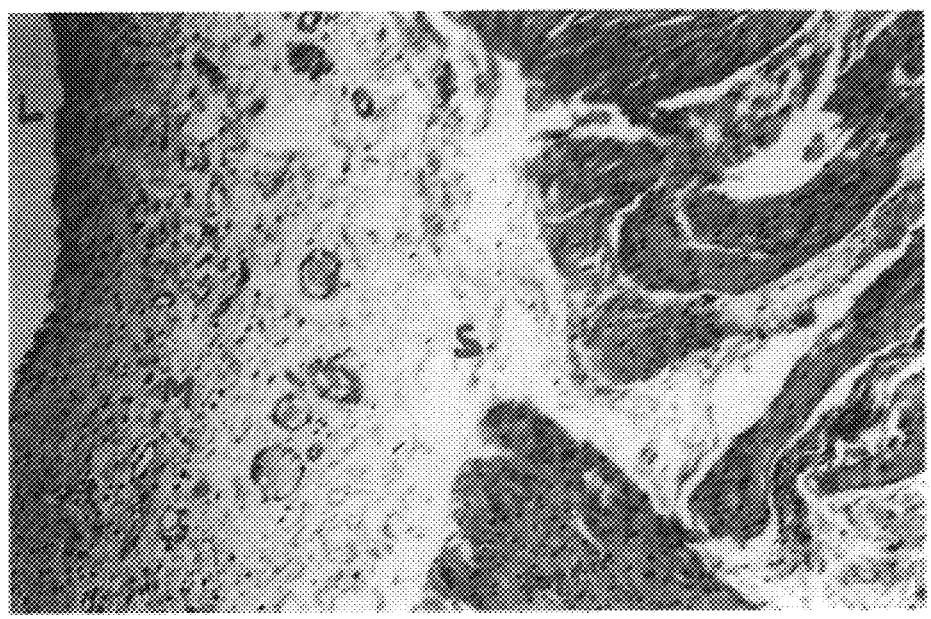

FIG. 17: Urinary Bladder Continued: Isolated membrane mucosal side of lumen (L). Smooth muscles (M) are sparce in three months post operative period but properly developed (SM submucosa).

Figure 18:
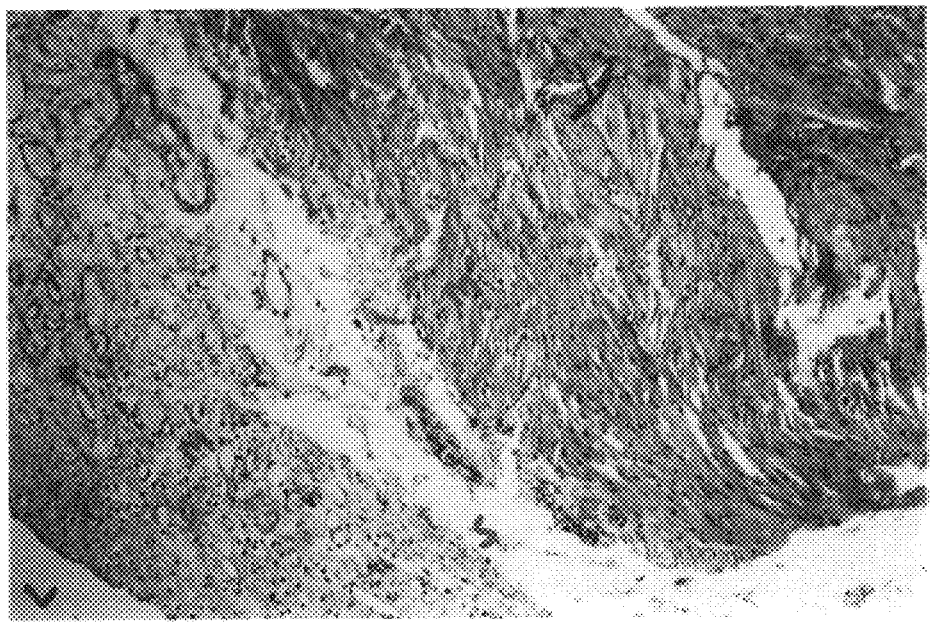

FIG. 18: Normal Urinary Bladder: Histology: H&E stain, 10×10 magnification note the smooth muscles in comparison to neo-regenerated. Smooth muscles smooth muscles are closely knit in normal but sparce in neo-regenerated urinary bladder.

I. REGENERATION OF BILE DUCT i) Development of Common Bile Duct, Gall Bladder and Liver in an Embryo:

In an embryo, liver, gall bladder and common bile duct develop from the hepatic bud which arises as an endodermal bud from ventral aspect of the gut at the juncture of fore-gut and mid-gut [FIG. 1A]. The bud grows into ventral mesogastrium and passes though the mesogastrium to enter septum transversum (FIG. 1B). It enlarges and soon shows two part is the larger is part is pars hepatica and smaller is pars cystica (FIG. 1 C(i) and (ii)). These buds give rise to liver and gall bladder respectively (FIG. 1D). The duct proximal to pars cystica forms the common bile duct. It opens on the ventral aspect of gut—the developing duodenum. Later with differential of growth of duodenal wall and the rotation of duodenal loop, it curves to open on the dorso medial aspect of the duodenum alongwith pancreatic duct.

The pluripotent stem cells of endodermal original exist in bases of crypts of gastro-intestinal tract in varied numbers from oesophagus to anus: There are gut proliferative zones in various regions of the gastro-instestinal tract which contain stem cells.(Fenoglio—Preiser C M, Noffsinger A E, Stemmermann, G. K. Lavitz P. E., Listrom, M. B., Rilke F O. "General features of G.I.T., Ch. I, $2^{nd}$ Edn. Gastro intestinal pathology" An Atlas and Text; publishers: Lippincott—Raven, Philad, NY. P. 1–14=199). These cells have the capacity to give rise to several types of differentiated cells, i.e. it is multipotent and are capable of maintaining differentiation cell potential.

Thus, the bile duct and duodenum originate in neighbouring regions from the same embryonal germ layer, i.e. the endoderm. The applicant realised that the cells in the tissues belong to endodermal germ layers of primitive gut of developing embryo and are therefore, committed to develop into tissues and organs that have evolved from the endoderm. Environmental influence, functional need of the region, local tissue cytokins of the anatomical site may stimulate these cells to undergo differentiation and proliferation and maintain tissues in that site. Accordingly, the applicant has isolated a membrane containing pluripotent stem cells from the duodenal part of the gastroinstestinal tract, and used the potential of these cells to the regenerate bile duct.

ii) Regeneration of Bile Duct: Procedure:

The regeneration of bile duct was carried out in dogs. A segment of the duodenum is isolated by ligating blood vessels between the medial aspect of "C" curve of duodenum and the head of the pancreas as shown in FIG. 1E. A 2–3 inch segment of the duodenum is separated from the pancreas. This segment is excised between occlusion clamps at both ends of isolated segment. Duodenal continuity is established by anastomosing both cut ends of duodenum by known methods. A leak proof anastomosis is essential. In fact, any part of the duodenum can be selected but the part it is preferred to select a part which least interferes with the normal functioning of the duodenum.

The excised segment of duodenum is kept in normal saline and washed thoroughly to free the segment of its contents. The segment is ensleeved on a conical centrifuge tube as shown in FIG. 2. (used for easy insertion of tapering end of tube into duodenal lumen). Muscularis externa, serosa and part of sub mucosa (outer most) is excised along the entire circumference and whole length of duodenal segment. The duodenal cylinder is turned inside out and now the mucosa of the duodenal segment is excised along the entire length and circumference. The duodenal tube is turned outside in so that mucosal surface faces the lumen again. All free or teethered tags of muscle and mucosa removed. Care is taken to ensure that the crypts of intestine in muscularis mucosa layer remain intact. This is achieved by careful superficial dissection only. The perforation of the duodenal cylinder is avoided during dissection. Thus, a duodenal cylinder consisting of muscularis mucosa along with the bases of crypts having stem cells and part of sub-mucosa is obtained as shown in FIGS. 3 and 4. The sub-mucosa has loose areolar tissues with blood vessels, lymphatics, nerves etc. The cellular details of the membrane harvested is confirmed under the microscope as shown in FIGS. 4 & 5.

The membrane thus developed is a very tough membrane and can hold sutures very well. If the cells are distorted, undergone hydrolysis or damaged by direct trauma, chemicals, antibiotics, etc. then that layer becomes useless and is discarded. A thorough wash with saline is sufficient to ensure reasonable sterility of the harvested membrane.

A tube is constructed from this developed and isolated membrane, which is a little bigger than the outer diameter of common bile duct as shown in FIG. 6. This is anastomosed with spatulated proximal and distal cut ends of common bile duct left after excision of 1½ to 2" of common bile duct below the cystic duct junction as can be seen in FIGS. 7 and 8. A "T" tube is passed through an opening in normal bile duct, just proximal or distal to anastomotic sites. The horizontal limb is kept as stent in the membrane tube for three months. The vertical limb of "T"-tube is brought out through separate stab incision as shown in FIG. 8A. After 3 months, the grafted tube along with part of normal bile duct is excised and subjected to test the patency and histological examination.

(iii) Gross Examination:

When the abdomen was re-opened after three months, gross-examination revealed no collection of fluid, bile, serum blood inflammatory exudate or intestinal contents at the site of graft and sub hepatic region or in the general peritoneal cavity. This can be seen in FIG. 9. Mild adhesions were present which could be easily separated. The graft looked absolutely healthy. No shrinking or contraction of tube was observed. No fibrosis or stricture was seen on examination.

The excised tube graft was healthy and colour of graft was comparable to that of normal bile duct. The length of graft remained same after 3 months of grafting in vivo. The thin transparent look of duodenal membrane cylinder (i.e. the autogenous membrane) disappeared. The wall showed substantial gain in thickness.

Mucosal surface was smooth and glistening. No ulcer or any abnormality was observed. The surface was comparable with that of normal bile duct. The mucosal surface of graft was continuous with that of normal bile duct.

(iv) Microscopic Examination (A) Duodenal Cylinder before graffing—developed membrane (shown in FIGS. 4 and 5), revealed the following layers in H & E stain:
1. Loose areolar tissue along with blood vessels, lymphatics, nerves to and fro from mucosa. This loose areolar tissue is a part of submucosa only.
2. Thin layer of muscularis mucosa.
3. Part of epithelium in the immediate viscinity to muscularis mucosa containing cellular element. The multiple circular and half moon like structures and cell groups were visible under microscope. If these cells are hydrolysed or traumatised or have lost configuration, the membrane is unsuitable for regeneration and is discarded. The cellular component of bases of crypt is an important layer of the membrane and is the cellular compartment of the developed duodenal cylinder. These cells belong to the bases of crypts of intestines and have pluripotent stem cell character.

(B) Histology of graft (i.e. the grafted membrane) after 3 months of in vivo colonization as shown in FIGS. 10 and 11 revealed the following in H&E Stain:
(i) At the junction of normal bile duct and graft membrane, fibromuscular tissue was observed. The fibrous element was more compared to muscular tissue. Smooth muscle cells were less as compared to main graft area at the centre of the graft. Smooth muscle changes were seen all over the graft area.
(ii) M.T.S. (Masson's Trichrome Strain) Fibrous tissue in green and smooth muscle cells in pink confirm the findings of H & E stain above.
(iii) Centre of the graft: H & E Stain. The graft showed more smooth muscle cells compared to the anastomotic site. Inflammatory cells were much less in the centre of graft as compared to anastomosed sites at the junction with normal bile duct.

All the layers of common bile duct were seen on the harvested duodenal membrane graft, i.e. muscosa, and fibromuscular wall with muscular fibres embedded in fibrous elements as shown in FIGS. 10 and 11.

II. REGENERATION OF URINARY BLADDER (i) Background:

In the embryo, urinary bladder is developed from the Cloaca, a part of the hind gut, by growth of an Uro-rectal septum This, septum separates cloaca into Uro-genital Sinus (UGS) and Rectum. This is shown in FIG. 12(i) and (ii). During $4^{th}$ and $7^{th}$ weeks of development, Uro Rectal Septum divides cloaca into Anorectal Canal and urogenital sinus. Upper and larger part of U.G.S. is urinary bladder. Lower and smaller and narrow part forms Urethra Trigone of urinary bladder is developed from mesonephic ducts and have developed from the germ layer mesoderm. The muscular and serous walls of the organ are derived from splanchnopleuric mesoderm. Cranial part of vesico urethral canal forms the epithelium of urinary bladder which is an endodermal derivative. UGS gives rise to urinary bladder of developed body. In fact, hind gut and Urinary Bladder are developed from same endoderm tissue in contiguous regions. Therefore, the stem cells of the hind gut are isolated and used for neo-regeneration of Urinary Bladder.

(ii) Regeneration of Urinary Bladder: Procedure:

A segment of the hind-gut (rectosigmoid junction) is isolated. Blood vessels are ligated and the segment is excised. The gut continuity is established by colorectal anastomosis. Excised hind-gut is thoroughly rinsed with copious saline solution and stored in saline. The serosa, muscularis extema, part of submuosa and mucosa carefully excised and a membrane cylinder was isolated in a similar manner as described for bile duct regeneration. The cylinder is slit longitudinally and is converted into a sheet of membrane containing pluripotent stem cells present in the bases of crypts as shown in FIG. 12A. The whole thickness of urinary bladder was extensively excised leaving trigone and ureteric openings intact as shown diagrammatic representation in FIG. 12B(i) to (iii). The photographic view is shown in FIGS. 14 and 15.

The isolated membrane is sutured with remnant of urinary bladder with intact trigone and ureteric openings. The anastomosis is made leak proof.

The capacity of newly constructed bladder is assessed by injecting same amount of saline as measured in normal urinary bladder before excision. The anastamotic site is identified by placing markers as shown in FIG. 13.

(iii) Post-Operative:

On re-exploration of isolated membrane graft on urinary bladder after 3 months, no collection of urine, serum, pus, intestinal contents at the site of bladder repair or intestinal anastomosis was observed. Omentum adhesion was seen in one of the dogs. Otherwise, the gross examination showed healthy look. The markers were all apart and showed no contraction except in one where omentum adhesion was seen. Remaining part of the graft was similar to the rest of the bladder wall. The graft lost its thin semitransparent look and showed thickness. After three months, the bladder surface could not be differentiated from normal bladder wall.

(iv) Histology of Grafted Isolated Membrane After 3-months, Post Operative:

Histologically, all the layers of the urinary bladder could be seen as developed ones as shown in FIGS. 16, 17 and 18. The serosal layer had developed. The smooth muscles were seen. But smooth muscles were sparse, as compared to normal bladder wall. The mucosa was well developed.

Thus, as can be seen from the above examples of regeneration of bile duct and urinary bladder, the applicant used stem cells from autogenous tissues which are endodermal in origin and have inherent capacity to undergo differentiation and proliferation into different tissues to repair the normal wear and tear of local tissues. Further, the applicant has adopted an effective surgical technique thereby transferring stem cells having the intrinsic capacity for transformation, to a site where the desired organ/tissue is to be regenerated. For example, duodenal stem cells are shifted to bile duct region (both developed from germ layer endoderm of developing embryo) so that neo-regeneration of bile duct can be successfully achieved. Therefore, in the present invention transfer of stem cells to the desired site is provided. Moreover, the applicant exposes the stem cells to a new functional need and a new environment which induces the stem cells to undergo transformation to desired change in the region, i.e., the desired metaplasia. In a typical case, for bile duct regeneration, membrane from the contiguous embryonic site, i.e. from duodenal region is transferred to excised bile duct region.

Once the stem cell grafts are implanted in the organ site to be developed, the period required for normal growth may vary depending upon the organ in question. For example, in case of urinary bladder, in the present invention, at the end of 2 months, sparse musculature was observed compared to normal and after another three months, total regeneration of bladder was observed.

All surgeries were performed under general anaesthesia and under prophylactic peri-operative antibiotics therapy and post-operatively, analgesics were used to relieve pain.

What is claied is:

1. An in vivo and in situ method of organogenesis of tissues or organs developed from an embryonal endodermal germ layer, comprising steps of surgically transferring an autogenous membrane containing stem cells to a site where the organ or tissue is to be regenerated, said autogenous membrane being selected from a corresponding contiguous embryonal segment in a developed body and providing a new functional need and tissue environment for regeneration of the desired tissue or organ.

2. A method as claimed in claim 1, wherein the organ to be repaired or regenerated developed from an endodermal layer of a germ disc of an embryo.

3. A method as claimed in claim 1, wherein the autogenous membrane is a membrane containing stem cells which are rendered free from an influence of local anatomical tissue environment and made available for differentiation and proliferation at the site where regeneration of the organ is desired.

4. A method as claimed in claim 1, wherein intrinsic factors including a messenger gene and genetic factors, inherent in the stem cells, are exploited for the regeneration of the desired tissue or organ.

5. A method as claimed in claim 1 wherein the organ or tissue to be regenerated are bile duct and urinary bladder.

6. A method as claimed in claim 1, wherein the step of providing a functional need includes creating a stress of new functional need of a tissue system of a new location to which the stem cells have been shifted, to induce desired metaplasia.

7. A method as claimed in claim 1, wherein a mucosal surface of isolated membrane is kept towards the lumen of the organ to be regenerated or repaired.

8. A method as claimed in claim 1, wherein a time period of 2 to 5 months is provided for the regeneration of organs or tissue from the autogenous membrane.

9. A method as claimed in claim 1, wherein a bile duct is regenerated from an autogenous membrane obtained from the duodenum.

10. A method as claimed in claim 1, wherein a support is placed inside the autogenous membrane to counter act an abdominal pressure exerted.

11. A method as claimed in claim 1, wherein the organogenesis of various tissues or organs incorporates finctions of tissue inducers, tissue organizers or both to achieve regeneration or repair of any tissue or organ into its proper size, shape and form to perform its inherent functions.

12. A method as claimed in claim 1, wherein ends of a tubular graft and a CBD are spatulated before anastomosis to avoid constriction at an anastomosed site.

\* \* \* \* \*